United States Patent
Hübner et al.

(10) Patent No.: US 9,255,157 B2
(45) Date of Patent: Feb. 9, 2016

(54) **RHAMNO-POLYSACCHARIDE FROM *ENTEROCOCCUS FAECIUM* CLONAL COMPLEX 17 AND USES THEREOF**

(75) Inventors: Johannes Hübner, Freiburg (DE); Christian Theilacker, Zürich (CH); Zbigniew Kaczynski, Gdansk (PL); Otto Holst, Bad Oldesloe (DE)

(73) Assignees: Universitaetsklinikum Freiburg, Freiburg (DE); Forschungszentrum Borstel, Borstel (DE)

( * ) Notice: Subject to any disclaimer, the term of this patent is extended or adjusted under 35 U.S.C. 154(b) by 80 days.

(21) Appl. No.: 14/122,820

(22) PCT Filed: May 25, 2012

(86) PCT No.: PCT/EP2012/059843
§ 371 (c)(1),
(2), (4) Date: Feb. 19, 2014

(87) PCT Pub. No.: WO2012/163833
PCT Pub. Date: Dec. 6, 2012

(65) Prior Publication Data
US 2014/0161792 A1    Jun. 12, 2014

(51) Int. Cl.
| | |
|---|---|
| *A61K 39/00* | (2006.01) |
| *A61K 39/02* | (2006.01) |
| *C08B 37/00* | (2006.01) |
| *A61K 31/702* | (2006.01) |
| *A61K 31/715* | (2006.01) |
| *A61K 39/09* | (2006.01) |
| *A61K 45/06* | (2006.01) |
| *C07K 16/12* | (2006.01) |
| *C07K 16/42* | (2006.01) |

(52) U.S. Cl.
CPC .............. *C08B 37/006* (2013.01); *A61K 31/702* (2013.01); *A61K 31/715* (2013.01); *A61K 39/09* (2013.01); *A61K 45/06* (2013.01); *C07K 16/1267* (2013.01); *C07K 16/4233* (2013.01)

(58) Field of Classification Search
CPC ..................................................... C08B 37/006
See application file for complete search history.

(56) References Cited

FOREIGN PATENT DOCUMENTS

WO    WO 99/08705    2/1999

OTHER PUBLICATIONS

Leavis et al (PLOS Pathogens vol. 3, Issue 1, pp. 75-96, 2007).*
Hsu, Carolyn et al., "Immunochemical characterization of polysaccharide antigens from six clinical strains of Enterococci," *BMC Microbiology*, Jul. 12, 2006, vol. 6:62, p. 1-9.
Huebner, Johannes et al., "Prophylactic and Therapeutic Efficacy of Antibodies to a Capsular Polysaccharide Shared among Vancomycin-Sensitive and-Resistant Enterococci," *Infection and Immunity*, Aug. 2000, vol. 68, No. 8, p. 4631-4636.
Ristl, Robin et al., "The S-Layer Glycome—Adding to the Sugar Coat of Bacteria," *International Journal of Microbiology*, 2011, vol. 2011, Article ID 127870, p. 1-16.
Theilacker, Christian et al., "Serodiversity of Opsonic Antibodies against *Enterococcus faecalis*—Glycans of the Cell Wall Revisited." *PLoS ONE*, Mar. 2011, vol. 6, Issue 3, e17839, p. 1-11.

* cited by examiner

*Primary Examiner* — Albert Navarro
(74) *Attorney, Agent, or Firm* — Saliwanchik, Lloyd & Eisenschenk

(57) ABSTRACT

The present invention relates to a rhamno-polysaccharide antigen from *Enterococcus faecium* clonal complex which is useful as a vaccine component for therapy and/or prophylaxis of bacterial infection.

8 Claims, 2 Drawing Sheets

RHAMNO-POLYSACCHARIDE FROM ENTEROCOCCUS FAECIUM CLONAL COMPLEX 17 AND USES THEREOF

CROSS REFERENCE TO A RELATED APPLICATION

This application is a National Stage Application of International Application Number PCT/EP2012/059843, filed May 25, 2012; which claims priority to European Application No. 11004387.4, filed May 27, 2011; both of which are incorporated herein by reference in their entirety.

The present invention relates to a rhamno-polysaccharide antigen from *Enterococcus faecium* clonal complex 17 which is useful as a vaccine component for therapy and/or prophylaxis of bacterial infection.

BACKGROUND OF THE INVENTION

Enterococci are among the most important pathogens associated with nosocomial infections. Especially *E. faecium* have acquired multiple antibiotic resistances and are often resistant to vancomycin, an antibiotic of last resort against multi-resistant Gram-positive bacteria. Furthermore, it has been shown that the determinant for vancomycin resistance can be transferred from *E. faecium* to the much more virulent *Staphylococcus aureus* (Chang et al. Infection with vancomycin-resistant *Staphylococcus aureus* containing the vanA resistance gene. N Engl J Med (2003) vol. 348 (14) pp. 1342-7). Specific lineages, such as the "clonal complex" 17, have been associated with hospital outbreaks of vancomycin-resistant *E. faecium* world-wide (Willems et al. Global spread of vancomycin-resistant *Enterococcus faecium* from distinct nosocomial genetic complex. Emerging Infect Dis (2005) vol. 11 (6) pp. 821-8) and these strains seem to be adapted particularly well to the hospital setting.

While some limited information exists regarding the presence and composition of capsular polysaccharides in *E. faecalis*, almost nothing is known about surface carbohydrates in *E. faecium*. Huebner et al. (Huebner et al. Isolation and chemical characterization of a capsular polysaccharide antigen shared by clinical isolates of *Enterococcus faecalis* and vancomycin-resistant *Enterococcus faecium*. Infect Immun (1999) vol. 67 (3) pp. 1213-9) could show that some *E. faecium* strains seem to be unencapsulated and are effectively killed by sera raised against lipoteichoic acid. However, a majority of strains seems to possess a capsule and are resistant to killing due to antibodies raised against enterococcal lipoteichoic acids (LTA) (unpublished observation).

Ristl et al. (in: Ristl R, Steiner K, Zarschler K, Zayni S, Messner P, Schäffer C. The s-layer glycome-adding to the sugar coat of bacteria. Int J Microbiol. 2011; 2011. pii: 127870. Epub 2010 Aug. 10) generally describe cell surface S-layer glycoproteins of Gram-positive bacteria. S-layer glycoproteins have the unique feature of self-assembling into 2D lattices providing a display matrix for glycans with periodicity at the nanometer scale. Typically, bacterial S-layer glycans are O-glycosidically linked to serine, threonine, or tyrosine residues, and they rely on a much wider variety of constituents, glycosidic linkage types, and structures than their eukaryotic counterparts. Ristl et al. report that no precise function could be attributed to bacterial S-layer glycoprotein glycans so far. The publication also describes the S-layer glycoprotein glycans of *G. stearothermophilus* NRS 2004/3a and *P. alvei* CCM 2051$^T$ as showcases to illustrate very recent data on the biosynthesis machinery governing S-layer protein glycosylation. The S-layer glycoprotein glycan of *G. stearothermophilus* as described contains a single α2-rhamnose-α3-rhamnose-α3-rhamnose unit. No antibodies or pathogenic bacteria are described.

Since there are often virtually no antibiotics available to treat patients with VRE infections, the development of alternative treatment options are of utmost importance. It is therefore an object of the present invention to provide new and effective antigens, and in particular polysaccharide (PS)-antigens, in order to develop new promising vaccines for an active or passive immunotherapy of bacteria, and in particular enterococci.

The present invention fulfils these needs by providing a rhamno-polysaccharide antigen from *E. faecium* clonal complex, comprising an antigenic structure of the following formula

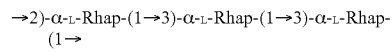

→2)-α-L-Rhap-(1→3)-α-L-Rhap-(1→3)-α-L-Rhap-(1→ wherein Rha is selected from rhamnose, and wherein optionally at least one group —OH is replaced by —OW, wherein W is selected from acetyl, $C_1$ to $C_{12}$-alkyl, and $C_1$ to $C_{12}$-alkenyl; and salts or solvates thereof. Preferably, Rha is selected from rhamnose. Preferably, the α2-rhamnose-α3-rhamnose-α3-rhamnose unit of the S-layer glycoprotein glycan of *G. stearothermophilus* is excluded.

In order to identify targets of opsonic antibodies in *E. faecium*, the inventors used a clinical isolate belonging to the clonal complex 17 (CC17) (*E. faecium* E155, Leavis et al. Insertion sequence-driven diversification creates a globally dispersed emerging multiresistant subspecies of *E. faecium*. PLoS Pathog (2007) vol. 3 (1) pp. e7) that was heat-killed (65° C. for 45 min) and injected into a rabbit. The resulting serum was tested in an opsonophagocytic assay, the best surrogate for a protective immune response against bacterial pathogens. The resulting sera showed a killing of 72% at a dilution of 1:20 against the homologous strain (see FIG. 2).

The rhamno-polysaccharide antigen of the invention provides a new and effective antigenic target for the development of more efficient strategies to effectively treat and/or prevent infection in vertebrates caused, at least in part, by enterococci or other Gram-positive bacteria, allows for improved vaccination strategies, and allows the development and production of respective vaccines, such as glycoconjugate vaccines.

The rhamno-polysaccharide antigen of the invention of the polysaccharide of *E. faecium* consists of a trisaccharide repeating unit according to the above formula. Thus, further preferred is a rhamno-polysaccharide antigen of the invention, wherein said antigen comprises 1 to 20 trisaccharide repeating units, preferably 1 to 10 units, such as, for example, at least 1, at least 2, at least 3, at least 4, at least 5, or at least 6, and most preferred 1 to 3 units. Further preferred are 2 to 20 units, such as, for example 2 to 5 or 2 to 10 units.

The above rhamno-polysaccharide antigen can furthermore include at least one (which is preferred) linker group L, which is preferably attached to one of the ends of the chain of the repeating unit(s) and/or the sugar moieties, in order to be coupled or conjugated to other chemical entities. These linker groups are known in the state of the art, and usually are immunologically inactive, i.e. do not interfere with the immunological properties of the rhamnopolysaccharide antigen. Preferred linkers include, but are not limited to, $C_1$ to $C_{12}$ alkylamino linkers, which are optionally substituted with other groups, or peptide linkers. Other modifications include the addition of chemical moieties to the rhamno-polysaccharide antigen (also included in "L") in order to carry a detectable label, such as chelating groups or enzymatic groups. Furthermore, peptide (e.g. His) or other "labels" or "tags" can be added in order to be able to purify and/or use the rhamno-polysaccharide antigen, for example in diagnostic assays.

Although it is speculated that the immunologic activity of said molecule increases with its length of rhamno-polysaccharide antigen units, the inventors assume that shorter molecules can already be quite effective in their immune response.

Another aspect of the invention then relates to a pharmaceutical composition, comprising at least one of the rhamno-polysaccharide antigens according to the present invention and/or at least one antibody according to the present invention as described below, together with at least one pharmaceutically acceptable carrier, adjuvant and/or diluent.

Particularly preferred is a pharmaceutical composition according to the present invention, wherein said composition comprises a rhamno-polysaccharide antigen as described herein.

Further preferred is a pharmaceutical composition according to the present invention, wherein said composition is formulated as a vaccine, in particular against infections caused by enterococci, in particular antibiotic resistant enterococci, such as VRE strains, preferably of E. faecalis or E. faecium, e.g. E. faecium clonal complex 17. Most preferred is a pharmaceutical composition according to the present invention, wherein said rhamno-polysaccharide antigen according to the present invention is present in a glycoconjugate vaccine.

The rhamno-polysaccharide antigen according to the present invention (either present as the antigen alone or in a bacterial extract or cell wall fraction) is preferably used for an enterococcal, staphylococcal, or pneumococcal vaccine, either for active or passive immunization.

Thus the invention further provides a pharmaceutical composition, and in particular a vaccine, for the prevention of enterococcal infections in a vertebrate, said pharmaceutical composition comprising at least one rhamno-polysaccharide antigen according to the present invention, optionally together with a pharmaceutically acceptable carrier, adjuvants and/or diluent. Preferred carriers include, but are not limited to, CRM (CRM197), *Tachypleus tridentatus* hemocyanin (TTH), *Limulus polyphemus* hemocyanin (LPH), tetanus toxoid (TT), diphtheria toxoid (DT), bovine serum albumin (BSA), and the ExoU protein.

Typically, the vaccine can further comprise live or dead intact cells of at least one enterococcal strain, preferably of *E. faecium*, together with the rhamno-polysaccharide antigen of the invention. More typically, the vaccine comprises cell lysate from at least one enterococcal strain. The methods for purifying the selected bacterial fractions containing enterococcal rhamno-polysaccharide antigen are known to the person of skill. Another aspect relates to a pharmaceutical composition or vaccine, wherein the rhamno-polysaccharide antigen as included has been produced, at least in part, through chemical synthesis.

Typically, the vertebrate is a monogastric, herbivore or ruminant animal or human subject. Even more typically, the vertebrate is selected from the group consisting of human, non-human primate, murine, bovine, ovine, equine, porcine, caprine, leporine, avian, feline and canine. More typically, the vertebrate is selected from the group consisting of human, ovine, camelids, porcine, bovine, equine or canine.

The pharmaceutical composition can be formulated for administration via intramuscular, subcutaneous, topical or other parenteral route. In general, the microorganisms of the present invention are commensal in nature. Thus, oral administration is generally not an effective route of vaccination, and as a consequence, administration via an intramuscular, subcutaneous topical or other parenteral route is preferred. Preferably, the vaccine is formulated for administration via intramuscular, subcutaneous, or inhalation routes. The vaccine may also include cytokines, such as: G-CSF, GM-CSF, interleukins or tumor necrosis factor alpha, used singly or in combination.

The pharmaceutical composition may also include an adjuvant. More typically, the adjuvant is selected from the group consisting of Freunds Complete/Incomplete Adjuvant, Montenide Macrol Adjuvant, Phosphate Buffered Saline and Mannan oil emulsions, saponins (QuiLA) dextran (dextran sulphate, DEAE-Dextran), aluminum compounds (Imject Alum), N-acetylglucosamiyl-N-acetylmuramyl-L-alanyl-D-isoglutamine (Gerbu adjuvant). More typically, the adjuvant is selected from the group as described in the Vaccine 1995, vol 13, page 1203; 1993 vol 11 page 293; and 1992 vol 10 page 427, the disclosures of which are incorporated herein by reference.

Yet another important aspect of the present invention then relates to the rhamno-polysaccharide antigen according to the present invention, the antibody according to the present invention, or the pharmaceutical composition according to the present invention for use in medicine and for the treatment of diseases, such as bacterial infections, in particular by a Gram-positive bacterium, such as, for example, bacterial infection, enterococcal infection, urinary tract infections, bacteremia, bacterial endocarditis, peritonitis, wound and soft tissue infections, and meningitis, or pneumonia, and foreign body infections. Said Gram-positive bacterium can be preferably selected from enterococci, staphylococci or streptococci, such as, for example, *E. faecium*, e.g. *E. faecium* clonal complex 17, *E. faecalis*, *S. aureus*, coagulase-negative staphylococci, *Pneumococcus*, or *S. pyogenes*, and in particular antibiotic-resistant strains thereof, such as VRE-resistant ones.

Another aspect of the invention then relates to a method for producing the rhamno-polysaccharide antigen of the invention, wherein said method comprises synthesizing said antigen through chemical synthesis, comprising, for example, solution phase and/or solid phase chemistry.

Preferred is a method for producing the rhamno-polysaccharide antigen according to the present invention, comprising synthesizing said molecule on a solid phase material. The methods of the present invention more preferably are in an automated solid-phase synthesis format.

Another aspect of the invention relates to an antibody, preferably a monoclonal antibody or antigenic fragment thereof, that specifically recognizes the rhamno-polysaccharide antigen according to the present invention. The term "antibody" shall include both monoclonal or polyclonal antibodies, recombinant antibodies or fragments thereof, such as Fab and the like, as well as human or humanized antibodies.

Another aspect of the invention then relates to a method for producing the antibody according to the present invention, comprising immunizing a mammal, preferably a rabbit, with the rhamno-polysaccharide antigen according to the present invention, or a with the pharmaceutical composition according to the present invention, or preferably the vaccine according to the present invention, and, optionally isolating said antibody from said animal. Respective methods are known to the person of skill, and are disclosed in the state of the art.

Yet another aspect of the present invention then relates to a method for producing a monoclonal antibody according to the present invention that is specific for the rhamno-polysaccharide antigen according to the present invention, comprising generating hybridoma cells producing said antibody as a monoclonal antibody, or comprising a recombinant production of said antibody in a host cell. Respective methods are known to the person of skill, and are described in the state of the art.

Yet another aspect of the present invention then relates to a method for producing an anti-idiotypic antibody that is specific for the antibody according to the present invention as described above. Another aspect of the invention then relates to said anti-idiotypic antibody, which can also be monoclonal or polyclonal antibodies, recombinant antibodies or fragments thereof, such as Fab and the like, as well as human or humanized antibodies.

Still another important aspect of the present invention then relates to the use of the rhamno-polysaccharide antigen according to the present invention as an antigen in the production of antibodies that are specific for said rhamno-polysaccharide antigen.

Yet another important aspect of the present invention then relates to the use of the rhamno-polysaccharide antigen according to the present invention, the antibody or anti-idiotypic antibody according to the present invention, or the pharmaceutical composition according to the present invention for the treatment against bacterial infections or for the production of a medicament for the prophylactic or therapeutic treatment of a disease or condition caused by bacterial infections, in particular enterococcal infection, such as nosocomial infection, bacteraemia, endocarditis, urinary tract infections, surgical wound infections, peritonitis, wound and soft tissue infections, meningitis, pneumonia, and foreign body infections, in particular caused by antibiotic resistant enterococci, such as VRE strains, such as *E. faecalis*, and also staphylococci and streptococci. Preferably, said medicament is a vaccine as described herein.

According to yet another preferred embodiment of the invention, there is provided a method for inducing an immune response against at least one Gram-positive bacterial strain, such as an enterococcal strain, comprising the rhamno-polysaccharide antigen of the present invention in a vertebrate, said method comprising administering to said vertebrate an immunologically effective amount of the vaccine in accordance with the invention, or a pharmaceutical composition in accordance with the invention.

According to yet another preferred embodiment of the invention, there is provided a method for treating or preventing a bacterial infection in a vertebrate, comprising administering to said vertebrate a therapeutically effective amount of the rhamno-polysaccharide antigen according the present invention, the antibody according to the present invention, or the pharmaceutical composition according to the present invention.

Preferred is a method according to the present invention, wherein said bacterial infection, in particular enterococcal infection, is a nosocomial infection, bacteraemia, endocarditis, urinary tract infections, surgical wound infections, peritonitis, wound and soft tissue infections, meningitis, pneumonia, or foreign body infections, in particular caused by antibiotic resistant enterococci, such as VRE strains, such as *E. faecalis*, staphylococci or streptococci.

The present invention will now be further described in the following preferred non-limiting examples with reference to the accompanying figures. For the purposes of the present invention, all references as cited herein are incorporated in their entireties.

EXAMPLES

Figure 2:
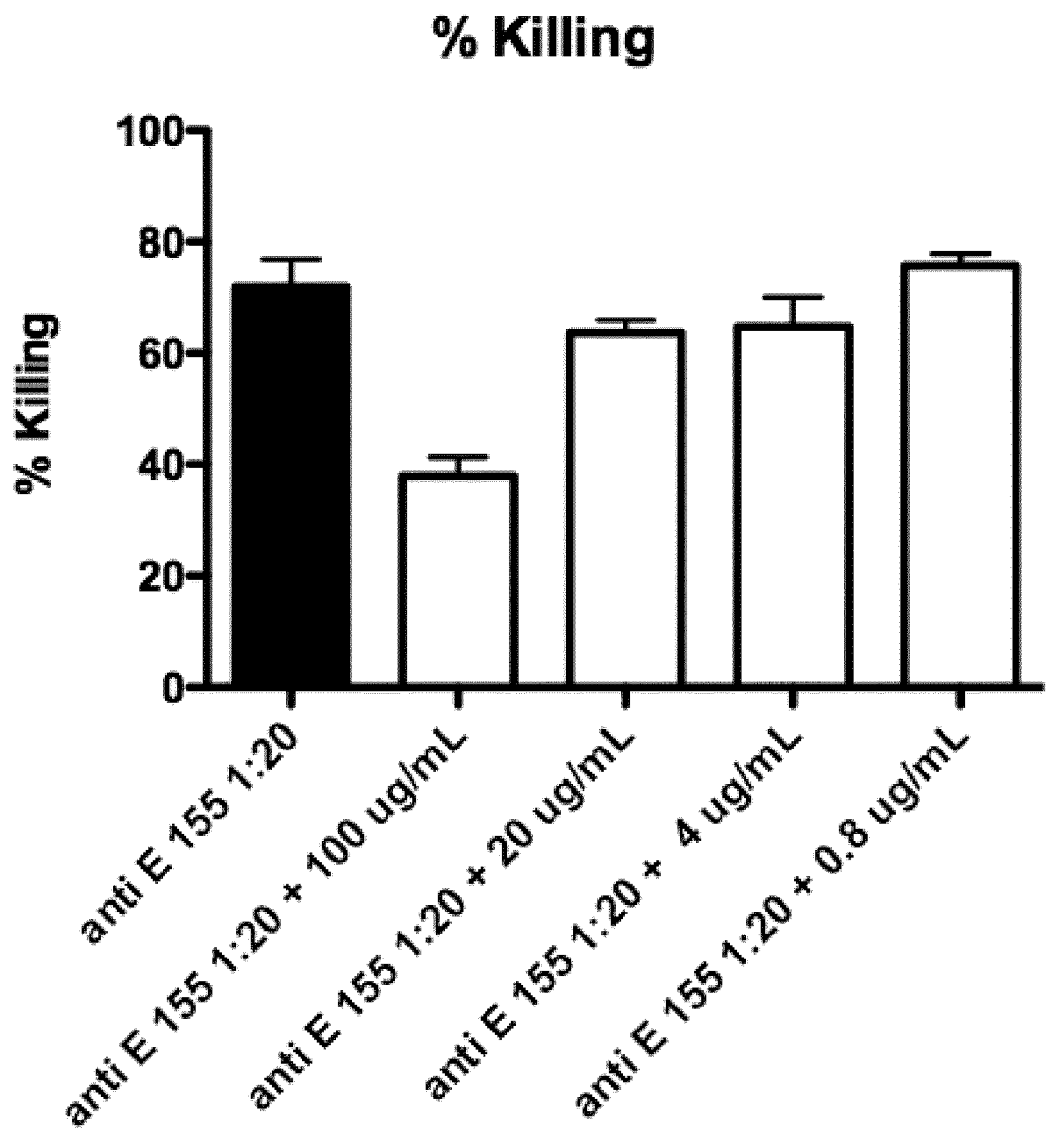
FIG. 2 shows opsonic killing of *E. faecium* 155 with rabbit serum raised against whole heat-killed bacteria, and inhibition of killing with different amounts of purified E155 rhamno-polysaccharide.

In order to identify targets of opsonic antibodies in *E. faecium*, the inventors used a clinical isolate belonging to the CC17 (*E. faecium* E155, Leavis et al. Insertion sequence-driven diversification creates a globally dispersed emerging multiresistant subspecies of *E. faecium*. PLoS Pathog (2007) vol. 3 (1) pp. e7) that was heat-killed (65° C. for 45 min) and injected into a rabbit. The resulting serum was tested in an opsonophagocytic assay, the best surrogate for a protective immune response against bacterial pathogens. The resulting sera showed a killing of 72% at a dilution of 1:20 against the homologous strain (see FIG. 2).

Bacteria were grown in Columbia broth supplemented with 0.5% glucose at 37° C. for 24 h. Bacterial cells were washed in PBS and cell walls were digested by addition of mutanolysin and lysozyme (each at 100 µg/ml in PBS supplemented with 20 mM $MgCl_2$, 20 mM $CaCl_2$, and 0.05% $NaN_3$) at 37° C. for 24 h. Insoluble material was removed by centrifugation, and the supernatant was treated with nucleases (DNase I and RNase A, 100 µg/ml) at 37° C. for 6 h followed by addition of proteinase K (100 µg/ml) at 59° C. for 24 h. The supernatant was dialyzed against deionized $H_2O$, and lyophilized. For size exclusion chromatography, the material was redissolved in $H_2O$, and applied to a column (1.0×90 cm) of BioGel P-100. Obtained polymeric fraction was dialyzed, lyophilized, resuspended in 20 mM $CH_3COONH_4$ (pH 8.0) and applied to an anion-exchange column (Q-Sepharose FF). Bound antigen was eluted from the column by a gradient of 1 M $CH_3COONH_4$ (pH 8.0) and fractions were assayed for hexose content, then pooled and controlled by $^1H$ NMR spectroscopy. Fractions eluted at the beginning of gradient were subjected to further chemical and NMR analyses.

Sugar analysis of obtained polysaccharide revealed the presence of Rha only. The absolute configuration of monosaccharides was established by GLC of (S,R)- and (S)-but-2-yl glycosides. This experiment demonstrated L-configuration of the Rha residues.

The $^1H$ NMR spectrum of PS showed three anomeric signals at δ 5.165 (residue A, $^3J_{H1,H2}$<2 Hz), δ 4.980 (residue B, $^3J_{H1,H2}$<2 Hz), and δ 4.906 (residue C, $^3J_{H1,H2}$<2 Hz) and signals characteristic of the protons of the methyl groups of 6-deoxysugars (δ 1.268, δ 1.269, and δ 1.232). These signals confirmed presence of Rha which was identified by sugar analysis results.

The TOCSY spectrum exhibited three different spin systems, which enabled the identification of all the proton signals belonging to all residues. The proton orders in all spin systems were assigned using the COSY spectrum. All $^1H$ and $^{13}C$ chemical shifts (see Table 1) were established using $^1H$, correlated $^1H$, $^1H$ (COSY and TOCSY), as well as correlated $^1H$, $^{13}C$ HSQC NMR experiments.

Anomeric configurations of monosaccharides were defined on the basis of $^1J_{C-1,H-1}$ coupling constants derived from $^1H$, $^{13}C$ HSQC NMR experiment (recorded without decoupling). The values of $^1J_{C-1,H-1}$ were ~173 Hz, which revealed the α-anomeric configuration of all residues. The six-membered rings of all monosaccharides were assigned by the lack of carbon atom signals in the δ ~83-88 in $^{13}C$ NMR spectrum.

The $^1H$, $^{13}C$ HSQC NMR spectrum showed three anomeric carbon signals at δ 100.69 (A), δ 102.06 (B), and δ 101.85 (C). This spectrum also contained the remaining sugar carbon resonances. Low-field shifted signals of carbon atoms demonstrated substitutions at C-2 of A (δ 78.04), C-3 of B (δ 77.73), and C-3 of C (δ 78.04) residues.

The sugar sequence within the trisaccharide repeating unit of PS was assigned from ROESY experiment, which exhibited inter-residual NOE contacts between following anomeric protons and corresponding glycosidically linked protons: A1/B3 (δ 5.165/3.853), B1/C3 (δ 4.980/3.792), and C1/A2 (δ 4.906/4.037).

Figure 1:
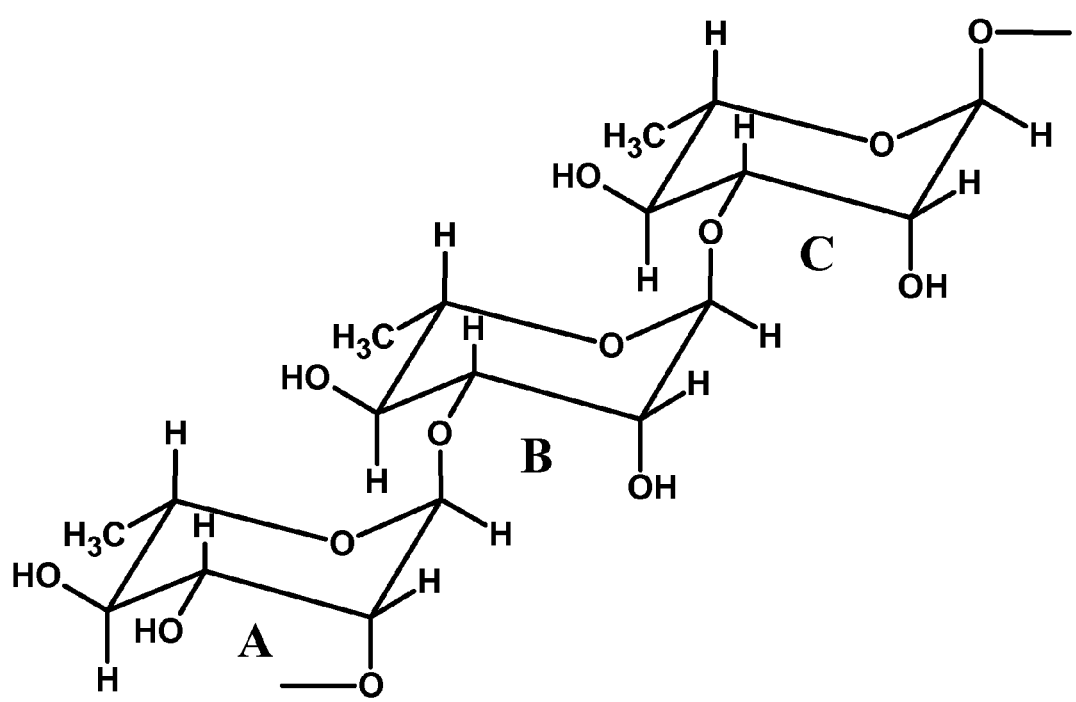
FIG. 1 shows the structure of the repeating unit of the PS according to the invention: →2)-α-L-Rhap-(1→3)-α-L-Rhap-(1→3)-α-L-Rhap-(1→.

Compositional analyses and NMR data revealed the structure of the repeating unit of the PS as shown in FIG. 1: →2)-α-L-Rhap-(1→3)-α-L-Rhap-(1→3)-α-L-Rhap-(1→

TABLE 1

| | | | | | | |
|---|---|---|---|---|---|---|
| $^1J_{C-1, H-1}$ [Hz] | H1 / C1 | H2 / C2 | H3 / C3 | H4 / C4 | H5 / C5 | H6 / C6 |
| →2-L-α-Rha (A) | 5.165 | 4.037 | 3.910 | 3.460 | 3.789 | 1.269 |
| 173 | 100.69 | <u>78.04</u> | 69.73 | 72.12 | 69.20 | 16.64 |
| →3-L-α-Rha (B) | 4.980 | 4.090 | 3.853 | 3.517 | 3.846 | 1.268 |
| 173 | 102.06 | 69.90 | <u>77.73</u> | 71.42 | 69.16 | 16.64 |
| →3-L-α-Rha (C) | 4.906 | 4.130 | 3.792 | 3.510 | 3.708 | 1.232 |
| 173 | 101.85 | 69.77 | <u>78.04</u> | 71.34 | 69.29 | 16.69 |

$^1$H and $^{13}$C NMR data chemical shifts of PS isolated from *E. faecium* E-155; Chemical shifts $^1$H and $^{13}$C [ppm] Residue The opsonic sera described above were absorbed with the rhamno-polysaccharide at different concentrations. A dose-depended inhibition of killing could be observed indicating that the rhamno-PS is the target of opsonic antibodies against *E. faecium* E155.

The invention claimed is:

1. A vaccine composition comprising a rhamno-polysaccharide antigen from *Enterococcus faecium* clonal complex, the antigen comprising the structure of the following formula

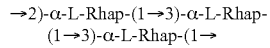
    (1→3)-α-L-Rhap-(1→ wherein Rha is rhamnose, and wherein optionally at least one group —OH is replaced by —OW, wherein W is selected from acetyl, branched or straight $C_1$ to $C_{12}$-alkyl, and branched or straight $C_1$ to $C_{12}$-alkenyl; and salts or solvates thereof, wherein the rhamno-polysaccharide antigen is conjugated to a chemical entity, optionally via a linker (L), and wherein the vaccine comprises a pharmaceutically acceptable carrier, adjuvant and/or diluent.

2. The rhamno-polysaccharide antigen from *Enterococcus faecium* clonal complex according to claim 1, wherein Rha is rhamnose, and salts or solvates thereof.

3. The rhamno-polysaccharide antigen according to claim 1, wherein said antigen comprises 1 to 20 trisaccharide repeating units.

4. The rhamno-polysaccharide antigen according to claim 1, wherein said L is attached to one of the ends of the chain and/or the sugar moieties of said antigen.

5. The vaccine composition according to claim 1, further comprising at least one cytokine.

6. The vaccine composition according to claim 1, wherein said adjuvant and/or diluent is suitable for administration of the vaccine via intramuscular, subcutaneous, or inhalation routes.

7. The vaccine composition, according to claim 3, wherein said antigen comprises 2 to 10 repeating units.

8. The vaccine composition of claim 1, wherein the carrier is selected from CRM197, *Tachypleus tridentatus* hemocyanin, *Limulus polyphemus* hemocyanin, tetanus toxoid, diphtheria toxoid, bovine serum albumin, and ExoU protein.

* * * * *